(12) United States Patent
Sawyer et al.

(10) Patent No.: US 8,771,684 B2
(45) Date of Patent: *Jul. 8, 2014

(54) METHOD OF USING SALMON THROMBIN TO ALLEVIATE PAIN

(75) Inventors: Evelyn S. Sawyer, Freeport, ME (US); Paul A. Janmey, Media, PA (US); Beth A. Winkelstein, Phila, PA (US)

(73) Assignee: Sea Run Holdings, Inc., Freeport, ME (US)

(*) Notice: Subject to any disclaimer, the term of this patent is extended or adjusted under 35 U.S.C. 154(b) by 0 days.

This patent is subject to a terminal disclaimer.

(21) Appl. No.: 13/208,479

(22) Filed: Aug. 12, 2011

(65) Prior Publication Data

US 2012/0009175 A1 Jan. 12, 2012

Related U.S. Application Data

(63) Continuation-in-part of application No. 12/582,040, filed on Oct. 20, 2009.

(60) Provisional application No. 61/393,678, filed on Oct. 15, 2010.

(51) Int. Cl.
| | |
|---|---|
| *A61K 38/48* | (2006.01) |
| *C12N 9/74* | (2006.01) |
| *C12N 5/00* | (2006.01) |
| *C12N 5/02* | (2006.01) |
| *A61F 13/00* | (2006.01) |
| *A61F 15/00* | (2006.01) |

(52) U.S. Cl.
CPC .................................. *A61K 38/4833* (2013.01)
USPC ........... 424/94.64; 435/214; 435/408; 602/48

(58) Field of Classification Search
None
See application file for complete search history.

(56) References Cited

U.S. PATENT DOCUMENTS

| | | | |
|---|---|---|---|
| 2002/0025921 A1* | 2/2002 | Petito et al. ...................... 514/2 |
| 2006/0095016 A1* | 5/2006 | Pauza et al. ................... 604/512 |
| 2010/0111926 A1* | 5/2010 | Winkelstein et al. ...... 424/94.64 |

OTHER PUBLICATIONS

Ju et al. Enhanced neurite growth from mammalian neurons in three-dimensional salmon fibrin gels. Jan. 26, 2007. Biomaterials. vol. 28, pp. 2097-2108.*

Michaud et al. Purification of salmon thrombin and its potential as an alternative to mammalian thrombins in fibrin sealants. 2002. Thrombosis Research. vol. 107, pp. 245-254.*

Wang et al. Purification of Salmon Clotting Factors and Their Use as Tissue Sealants, Thrombosis Research, vol. 100, 2000, p. 537-548.*

Manseth et al. Developing a Fish Meat-binding Agent: Purification of Salmon Thrombin. 2003. Journal of Food Science. vol. 68, No. 5, pp. 1648-1652.*

Balague et al. Non-specific low back pain in children and adolescents: risk factors. 1999. Eur Spine J. vol. 8, pp. 429-438.*

* cited by examiner

*Primary Examiner* — Anne Gussow
*Assistant Examiner* — Channing S Mahatan
(74) *Attorney, Agent, or Firm* — IP Strategies

(57) ABSTRACT

A method of alleviating pain associated with tissue damage includes applying salmon thrombin at a tissue damage site, as a single substance in liquid form, or as a powder, a foam, and/or a gel that includes salmon thrombin. A pain relief substance includes a salmon thrombin preparation.

38 Claims, 5 Drawing Sheets

METHOD OF USING SALMON THROMBIN TO ALLEVIATE PAIN

CROSS-REFERENCE TO RELATED APPLICATIONS

This is a continuation-in-part of co-pending U.S. patent application Ser. No. 12/582,040, which was filed on Oct. 20, 2009. Claim is also made of the benefit of the filing date of U.S. Provisional Patent Application No. 61/393,678, filed on Oct. 15, 2010, pursuant to 35 U.S.C. §119(e).

FIELD OF THE INVENTION

The invention relates to a therapeutic intervention to reduce nociceptive pain, especially the pain that results from stimulation of sensory receptors in the peripheral nervous system.

BACKGROUND OF THE INVENTION

Winkelstein et al. (2009) demonstrated alleviation of pain after nerve-root injury followed by application of salmon thrombin and salmon fibrin to the injury site. Nerve roots sit at the junction of the peripheral nervous system (PNS) and central nervous system (CNS) and contain elements of both systems. Therefore, CNS-mediated pain includes pain that could originate in either or both systems. Evidence was presented that the salmon-derived material was beneficial for pain resulting from injury to a nerve.

The present invention extends Winkelstein et al. by demonstrating a method of alleviating pain originating from tissue damage. This nociceptive pain in the peripheral nervous system signals the spinal cord and brain, and is therefore also CNS-mediated. Nociceptive pain includes the well-documented stimulation of peripheral pain fibers such as A- and C-fibers after surgery or other injury to skin, fascia, muscle, and bone.

Thrombin polymerizes fibrinogen to form a clot (fibrin) and is generally recognized as a hemostatic agent. Previous studies have shown that salmon thrombin and human thrombin are interchangeable for fibrin formation. Michaud et al 2002, emphasize the similarities of human and salmon thrombins. Comparison of these two thrombins showed similar primary structure and specific enzyme activity with respect to activation of fibrinogen, and therefore salmon thrombin performs well as a hemostatic agent (Rothwell et al. 2005). Hemostatic agents are indicated for many surgical procedures and injuries, and there is a wide selection available (Spotnitz al, 2008), but none address the accompanying pain. Bovine, human, and recombinant human thrombin are frequently used to control bleeding but these thrombins are pro-inflammatory in the CNS (Suo et al. 2004), and can in some cases exacerbate neuronal damage and pain (Wu et al, 2008). Thrombin can act on mammalian cells through protease activated receptors (PARs). The effect of these thrombin receptors on pain is complex, with some receptors on some cells inhibiting pain, and others promoting hyperalgesia (Garcia et al. 2010). In clinical practice however, mammalian thrombin is either ineffective for pain, or contraindicated as in cases of CNS injury. Therefore, the use of thrombin from any source as a treatment for pain is novel and represents a departure from current practice, which teaches against its use.

The pain of surgery and other tissue injury is most often treated with repeated injections of local anesthetics such as Marcaine® (bupivacaine), which can result in cardiovascular system toxicity (Mather, 2010), and opioids, which can lead to a host of problems including addiction. Therefore, there is a clear unmet clinical need for a safe, long-lasting, non-addictive substance for pain relief.

BRIEF SUMMARY OF THE INVENTION

According to an aspect of the invention, a method of alleviating pain associated with tissue damage includes applying salmon thrombin at a tissue damage site. The salmon thrombin can be applied as a single substance in liquid form. Alternatively, a powder, foam, gauze, and/or a gel that includes salmon thrombin can be applied. The method can be carried out by applying a combination of salmon thrombin with a substance such as platelet-rich plasma or fibrinogen from any source, preferably salmon fibrinogen and/or human fibrinogen. The substance can also include polyethylene glycol, a synthetic molecule preparation, collagen, and/or alginates. The substance can be applied, for example, by injection or spray.

The method preferably includes obtaining a salmonid that is a progeny of domesticated broodstock that are reared under consistent and reproducible conditions. Blood is obtained from the fish, plasma is separated from the blood, and the salmon thrombin is extracted from the plasma. Preferably, the salmonid from which the blood is obtained is sexually immature, in the log-phase of growth, larger than two kilograms, and/or reared by standard husbandry methods. The blood can be obtained from the salmonid by rendering the salmonid to a level of loss of reflex activity and drawing blood from a caudal blood vessel. Prior to rendering the salmonid to a level of loss of reflex activity, the levels of proteolytic enzymes and non-protein nitrogen present in the blood of the salmonid can be reduced. The plasma can be separated from the blood by centrifuging the blood. Extracting the salmon thrombin from the plasma can include performing an extraction process on the plasma such that all process temperatures are no greater than 6° C., no cytotoxic chemical residues remain in one or more plasma-components, and no oxidation of plasma lipids occurs. An antioxidant and/or a protease-inhibitor can be added to the plasma prior to extracting the salmon thrombin. Preferably, the salmonid is an Atlantic salmon.

Thrombin can be purified from either fresh or frozen plasma by prothrombin precipitations and chromatographic techniques.

Alternatively, the salmon thrombin can be obtained by fractionation.

Alternately, the salmon thrombin can be obtained by recombinant technology.

According to another aspect of the invention; a pain relief substance includes a salmon thrombin preparation. The preparation can also include fibrinogen, such as salmon fibrinogen, and/or polyethylene glycol, a synthetic molecule preparation, collagen, and/or alginates.

DETAILED DESCRIPTION OF THE INVENTION

The process preferably begins with the consistent and reproducible conditions under which donor fish are reared. All fish used as plasma sources preferably are progeny of domesticated broodstock, inspected for fish disease according to the American Fisheries Society "Blue Book" standards, sexually immature, in the log-phase of growth, larger than two kilograms, reared by standard husbandry methods, and fed a commercially pelleted food appropriate to the species.

Water temperature at the time of bleeding is preferably 4° C. to 12° C. The fish are preferably starved for five days before bleeding to reduce proteolytic enzymes and non-protein nitrogen. Each fish is stunned by a blow to the head, or by immersion in ice-water, or in water containing $CO_2$ or other fish anesthetic, in order to stun the fish to a level of loss of reflex activity (unconsciousness). Whole blood is then drawn from the caudal artery or vein with a sterile needle and syringe or vacuum tube containing an anticoagulant such as ACD (acid citrate dextrose), trisodium citrate, or other anticoagulant commonly used in human blood-banking.

Whole blood is held, preferably for no more than four hours at 2-4° C., and then centrifuged at 2-4° C. Thrombin then can be prepared by the method of Michaud et al., 2002.

Briefly, prothrombin is extracted from plasma with a series of barium chloride and ammonium sulfate precipitations. The prothrombin is activated by *Echis carinatus* venom, and the thrombin is passed over a heparin column. Thrombin is eluted from the column with a high salt buffer and frozen at <−60° C. The thrombin may then be lyophilized. Alternately, plasma fractionation or recombinant techniques can be used. These techniques are illustrative of those currently in use, but other techniques for preparation of thrombin or its precursor prothrombin may be equally effective.

Figure 1:
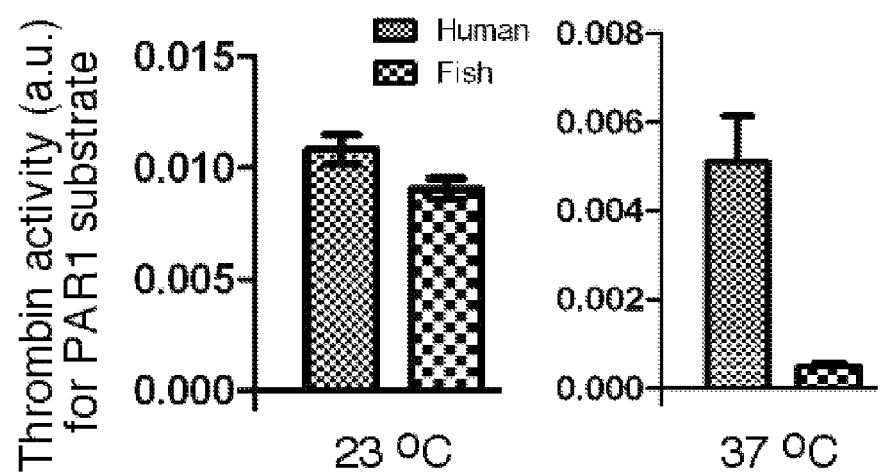
FIG. 1 is a chart showing the relative rates at which salmon thrombin and human thrombin cleave tetrapeptides based on the activation sites of PAR1.

Although mammalian thrombins are contraindicated for treatment of pain, we have found that salmon-derived thrombin is highly effective for pain originating from injury to nerves and other tissue. The beneficial effects of salmon thrombin are likely related to differing cellular receptors. In contrast to the very similar reactivity of salmon and human thrombin to fibrinogen-based substrates (Michaud et al. 2002), we have found substantial differences in their ability to activate protease activated receptors (PAR)s, as shown in FIG. 1, a chart demonstrating the relative rates at which salmon and human thrombin cleave tetrapeptides based on the activation sites of PAR1. At 37° C. salmon thrombin cleaves PAR1 approximately three times more slowly than human thrombin (p=0.0013). These findings illustrate some of the functional differences in mammalian and salmon thrombin.

Salmon thrombin is an effective hemostat (Rothwell et al., 2005), and the pain of serious injury is frequently accompanied by bleeding. Therefore, a thrombin that would treat both bleeding and pain would be highly beneficial.

The rat models that we have used in Examples #1-3 discussed below are widely accepted and predictive of human pain. An increase in latency for paw withdrawal after heat stimulus is especially indicative of reduced C-fiber activity that drives the spontaneous pain following surgery. Decrease in flexion or elevation of the injured paw is indicative of pain mitigation after the severe tissue and bone injury of Example #3. In these models, we have shown that a single administration of salmon thrombin to the site of injury results in significant acute and sustained (up to 48 hour) pain relief. This effect represents a vast improvement over the need for repeated injection of local anesthetics and the problems associated with prolonged opioid use.

EXAMPLE #1

As an example of nociceptive pain involving the PNS, we chose a rat incisional model of post-surgical pain. The rat plantar-incision model is a well-accepted and validated model that allows investigation of analgesia by comparing the effects of test substances during or after surgery (Whiteside et al. 2004; Brennan et al, 1996). Lyophilized salmon thrombin was rehydrated and held on ice for less than 4 hours before use. Rats were anesthetized with isoflurane (2-3%) vaporized in a nose-cone. The plantar left hind paw was prepared in a sterile manner with an iodine solution and 70% ethanol. A 1 cm-long incision starting 0.5 cm from the heel and extending toward the toes was made with a number 10 blade, through the skin and fascia of the plantar aspect of the paw including the underlying muscle (Brennan et al. 1996; Brennan 1999). The plantaris muscle was then elevated and longitudinally incised, leaving the muscle origin and insertion intact. The wound was blotted with a gauze pad and 50 μl salmon thrombin (10, 100, or 900 Units/ml) and a control (distilled water) was applied directly to the wound cavity. The skin was then closed with two mattress sutures of 5-0 nylon. At the end of surgery anesthesia was stopped, and rats were allowed to recover before being returned to their cages.

Figure 2:
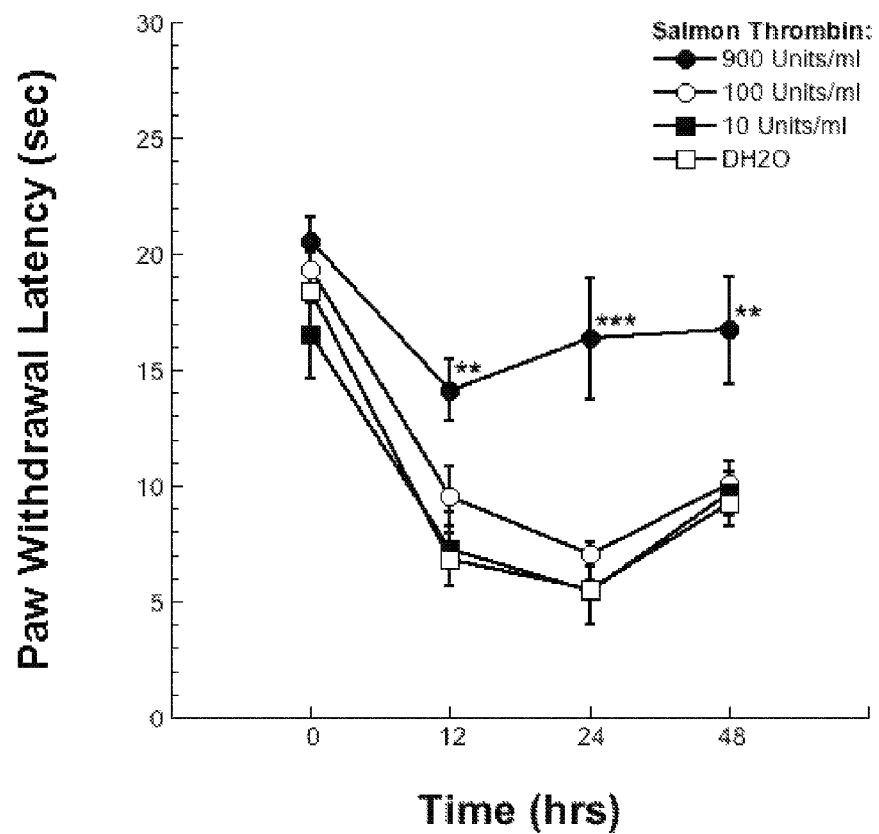
FIG. 2 is a chart showing paw withdrawal latency in 4 groups of rats after injury and treatment.

Before surgery and 12, 24, and 48 hours after surgery, groups of rats (N=4-6) were tested for pain using the thermal hyperalgesia method of Hargreaves et al. (1988). Briefly, rats were acclimated to a Plexiglass holding chamber that rests on a temperature-regulated glass surface. A heat source was focused through the glass unto the plantar surface of the injured paw. Upon paw withdrawal, the heat stimulus was deactivated and the rat's latency to withdrawal was measured to the nearest 0.1 seconds. Each animal latency score was an average of two trials separated by at least 5 minutes. In the absence of a response after 40 seconds, the test was terminated to prevent tissue damage. A two-way ANOVA was used to assess statistical significance. Results are shown in FIG. 2 as the paw withdrawal latency (number of seconds before paw is withdrawn) in 4 groups of rats (N=6) after incisional injury and treatment with salmon thrombin and distilled water (control). Pain, as taken by paw withdrawal latency, is significantly less than controls in salmon-thrombin treated animals (*$p<0.05$, $p<0.01$, *$p<0.001$).

Application of salmon thrombin significantly reduced pain, a dose-related reversal of thermal hyperalgesia as shown by paw withdrawal latency at 12 and 48 hours ($p<0.01$) and at 24 hours ($p<0.001$). All groups gained weight, and the treatment was well tolerated as assessed by behavioral observations.

EXAMPLE #2

Surgery on rats was similar to Example #1, but additional treatment groups (N=6) were added. Groups were:
(1) salmon thrombin, 50 μl of 1000 Units/ml
(2) human thrombin, 50 μl of 1000 Units/ml
(3) salmon fibrin bandage 1:4 (100 mg salmon fibrinogen and 100 Units thrombin)
(4) salmon fibrin bandage 1:8 (100 mg salmon fibrinogen and 50 Units salmon thrombin)
(5) control (distilled water DH2O)

Figure 3:
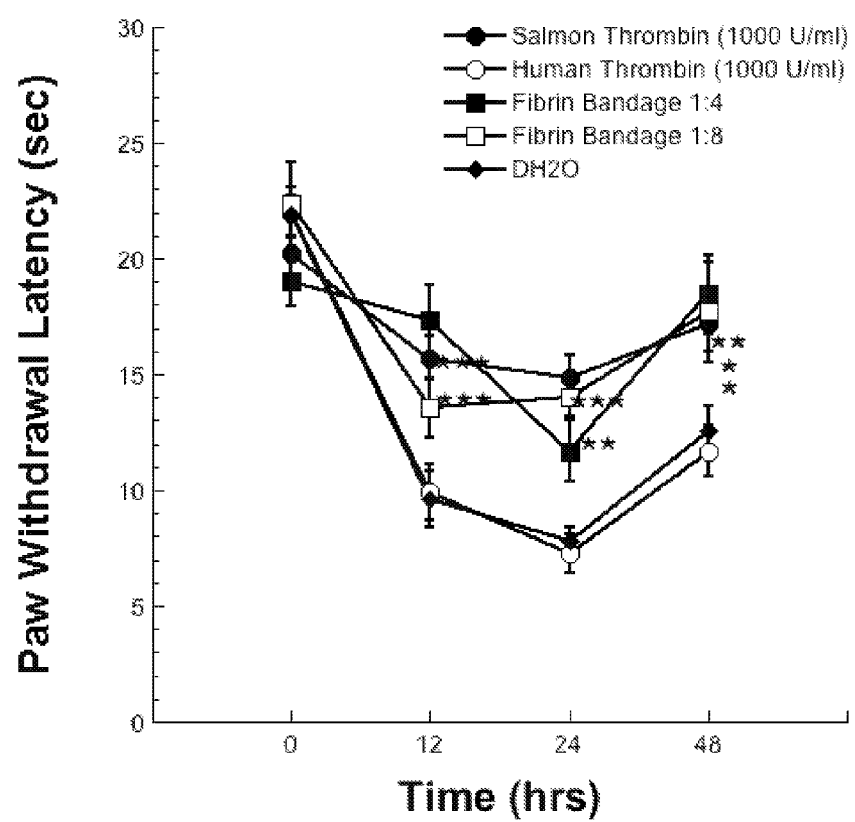
FIG. 3 is a chart showing paw withdrawal latency in 6 groups of rats (N=6) after injury and treatment.

Testing for thermal hyperalgesia was conducted as in Example #1 and showed a significant ($p<0.001$) reversal of thermal sensitivity for all of the salmon thrombin or fibrin treatments. Addition of salmon fibrinogen did not provide additional pain reversal compared to salmon thrombin alone. Human thrombin was similar to the control in providing no relief from thermal stimulation. Results are shown in FIG. 3 as paw withdrawal latency in 6 groups of rats (N=6) after incisional injury and treatment with salmon thrombin, salmon fibrin (salmon fibrinogen and thrombin), human thrombin, and distilled water. Pain, as taken by paw withdrawal latency, is significantly less in salmon thrombin and salmon fibrin-treated animals than in those treated with human thrombin or controls.

EXAMPLE #3

The rat model we used for this example is a modification of the Brennen/Whiteside model used for Examples #1 and #2. This injury to both soft tissue and bone is substantially greater than the first model, and produces severe pain. On a scale of 1-4 for subjective pain rating, Houghton et al. rated this model as a 4. In addition to the soft tissue injury, a hole was drilled in the calcaneus bone (Houghton et al. 1997) and salmon thrombin or distilled water applied to the injury site immediately after surgery. Another group of rats received subcutaneous morphine immediately after surgery at 5.6 mg/kg bodyweight.

Pain was evaluated by the thermal hyperalgesia model as in Example #1 and #2, and by the flexion/elevation test. The latter has been commonly used as an endpoint for studies of nociception, and has been validated as a measure of postoperative pain in rats (Roughan and Flecknell, 2001). Testing for hind limb flexion/elevation of the injured paw was quantified by the number of occurrences in 5 minute intervals over a span of 30 minutes (six readouts per testing time point), with a greater frequency of occurrences indicating more pain. An occurrence was defined if either flexion or elevation is apparent. A two-way ANOVA was used to determine statistical significance.

Figure 4:
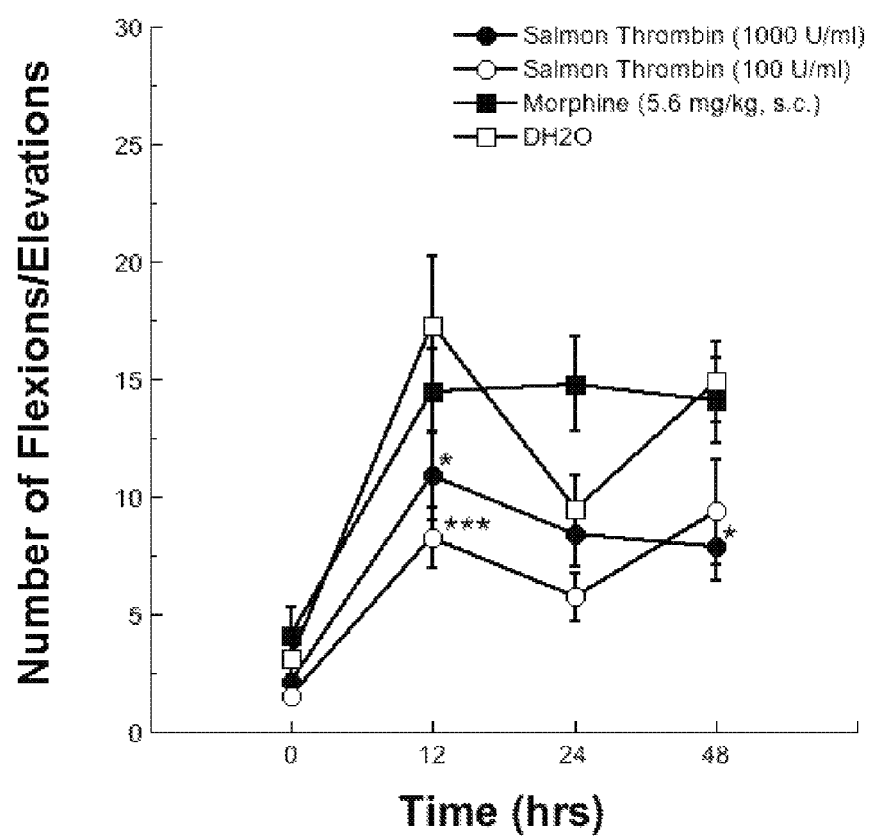
FIG. 4 is a chart showing flexion/elevation of the rat paw after bone injury and treatment.

FIG. 4 shows the flexion/elevation of the rat paw after bone injury and treatment with salmon thrombin, morphine, and distilled water. Pain as shown by this model was less for salmon thrombin-treated animals than for morphine-treated animals or the control group. The number of hind limb flexion/elevations was significantly less in salmon thrombin-treated animals than in the controls (*$p<0.05$, ***$p<0.001$).

Figure 5:
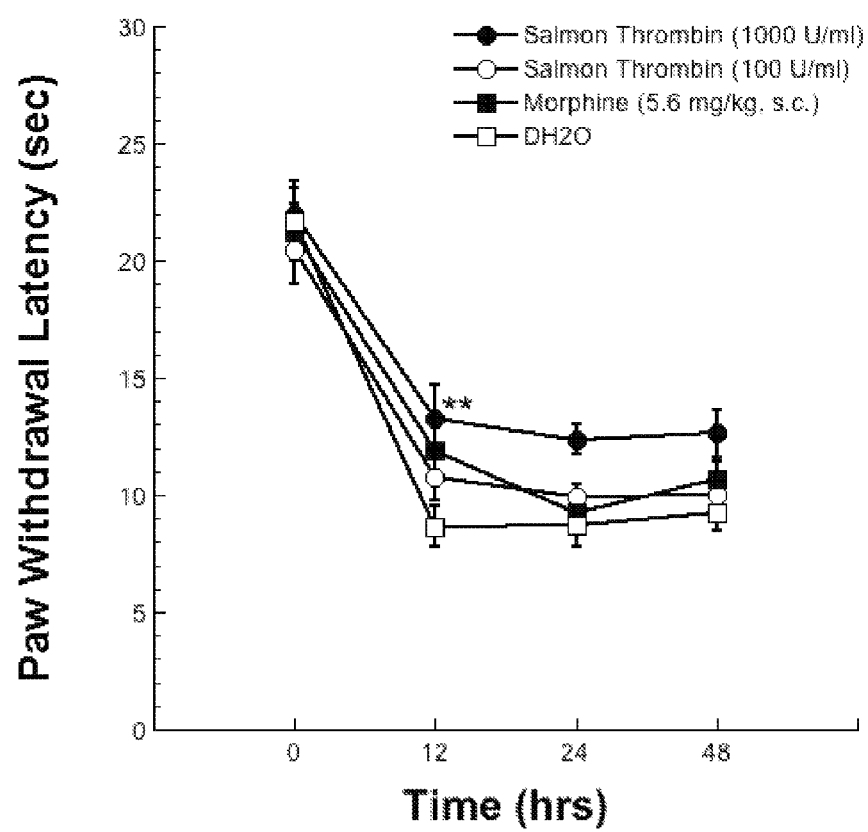
FIG. 5 is a chart showing paw withdrawal latency in 4 groups of rats after bone injury and treatment.

FIG. 5 shows the paw withdrawal latency (number of seconds before paw is withdrawn) in 4 groups of rats after bone injury and treatment with salmon thrombin, morphine, and distilled water. Pain, as taken by paw withdrawal latency, is significantly less ($p<0.01$) than controls in salmon thrombin-treated animals. Although the level of significance was not as great as in the soft tissue injury, this bone injury model produces a more severe pain.

Thus, application of salmon thrombin at the time of this tissue and bone injury significantly reduced pain as compared to controls. Testing for thermal hyperalgesia was conducted as in Examples #1 and #2 and showed a significant ($p<0.01$) reversal of thermal sensitivity. Flexion/elevation of the injured limb was significantly ($p<0.001$) less for salmon thrombin treated animals than for controls.

Although we applied the salmon thrombin as a single substance in liquid form, it may be used in other forms such as powder, foam, or gel, and with other materials such as gauze, foams, platelet-rich plasma, or fibrinogen from any source.

Thus, the present invention provides a method and substance for providing pain relief. A one-time application of salmon thrombin is safe, effective, and long-lasting, and works at least as well as other pain-relief substances without having addictive properties or requiring multiple treatments—contrary to other pain therapeutics.

The present invention has been described by way of example and in terms of preferred embodiments. However, it is to be understood that the present invention is not strictly limited to the particularly disclosed embodiments. To the contrary, various modifications, as well as similar arrangements, are included within the spirit and scope of the present invention. The scope of the appended claims, therefore, should be accorded the broadest possible interpretation so as to encompass all such modifications and similar arrangements.

REFERENCES

Brennan T J, Vandermeulen E P, Gebhart G F. 1996. Characterization of a rat model of incisional pain. Pain 64:493-501.
Brennan T J. 1999. Postoperative models of nociception. ILAR Journal 40(3):1-9.
Garcia P S, Gulati A, Levy J H. 2010. The role of thrombin and protease-activated receptors in pain mechanisms. Thrombosis and Hemostasis 103(6):1145-1151.
Hargreaves K, Dubner R, Brown F, Flores C, Joris J. 1988. A new and sensitive method for measuring thermal nociception in cutaneous hyperalgesia. Pain 32(1):77-88.
Houghton A K, Hewitt E, Westlund K N. 1997. Enhanced withdrawal responses to mechanical and thermal stimuli after bone injury. Pain. 73(3): 325-37.
Mather L E. 2010. The acute toxicity of local anesthetics. Expert Opin Drug Toxicol. 6(11):1313-32.
Michaud S E, Wang L Z, Korde N, Bucki R, Randhawa P K, Pastore J J, Falet H, Hoffmeister K, Kuuse R, Uibo R, Herod J, Sawyer E, Janmey P A. 2002. Purification of salmon thrombin and its potential as an alternative to mammalian thrombins in fibrin sealants. Thrombosis Research. 107:245-254.
Rothwell S W, Reid T J, Dorsey J, Flournoy W S, Bodo M, Jamey P A, Sawyer E. 2005. A salmon thrombin-fibrin bandage controls arterial bleeding in a swine aortotomy model. J Trauma 59(1): 143-149.
Roughan J V, Flecknell P A. 2001. Behavioral effects of laparotomy and analgesic effects of ketoprofen and carprofen in rats. Pain 90:65-74.
Suo Z, Citron B A, Festoff B W. 2004. Thrombin: a potential proinflammatory mediator in neurotrauma and neurogenerative disorders. 2004. Curr Drug Targets Inflamm Allergy 3(1):105-114.
Spotnitz W D, Burks S. 2008. Hemostats, sealants, and adhesives: components of the surgical toolbox. Transfusion 48:1502-1516.
Wu J, Yang S, Xi G, Song S, Fu G, Keep R F, Hua Y. 2008. Microglial activation and brain injury after intracerebral hemorrhage. Acta Neurochir Suppl 105:59-65.
Whiteside G T, Harrison J, Boulet J, Mark L, Pearson M, Gottshall S, Walker K. 2004. Pharmacological characterization of a rat model of incisional pain. British J Pharmacology 141:85-91.
Winkelstein B A, Janmey P A, Sawyer E S. 2009. Method of using salmon thrombin to alleviate central nervous system-mediated pain. U.S. patent application Ser. No. 12/582,040.

We claim:

1. A method of alleviating nociceptive pain associated with tissue damage, consisting essentially of administering salmon thrombin at a tissue damage site to slow the rate of protease activated receptor 1 (PAR1) activation at the tissue damage site, as demonstrated by the relative rate at which salmon and human thrombin cleave tetrapeptides based on the activation sites of PAR1, thereby diminishing a degree of pain experienced at the site.

2. The method of claim 1, wherein administering salmon thrombin includes administering the salmon thrombin substantially alone in liquid form.

3. The method of claim 1, wherein administering salmon thrombin includes administering at least one of a powder, a foam, and a gel substantially composed of the salmon thrombin.

4. The method of claim 1, wherein administering salmon thrombin includes administering at least one of gauze, foam, and platelet-rich plasma combined with the salmon thrombin.

5. The method of claim 1, wherein administering salmon thrombin includes administering a substance that includes salmon thrombin, wherein the substance also includes fibrinogen.

6. The method of claim 5, wherein the fibrinogen is salmon fibrinogen.

7. The method of claim 5, wherein the substance also includes any one or more of polyethylene glycol, a synthetic molecule preparation, collagen, and alginates.

8. The method of claim 5, wherein administering the substance includes spraying the substance.

9. The method of claim 1, further comprising:
obtaining a salmonid that is a progeny of domesticated broodstock that are reared under consistent and reproducible conditions;
obtaining blood from the salmonid;
separating plasma from the blood; and
extracting the salmon thrombin from the plasma.

10. The method of claim 9, wherein the salmonid from which the blood is obtained is at least one of sexually immature, in the log-phase of growth, larger than two kilograms, and reared by standard husbandry methods.

11. The method of claim 9, wherein obtaining blood from the salmonid includes:
rendering the salmonid to a level of loss of reflex activity; and
drawing blood from a caudal blood vessel.

12. The method of claim 11, wherein obtaining blood from the salmonid includes, prior to rendering the salmonid to a level of loss of reflex activity, reducing the levels of proteolytic enzymes and non-protein nitrogen present in the blood of the salmonid.

13. The method of claim 9, wherein separating plasma from the blood includes centrifuging the blood.

14. The method of claim 9, wherein extracting the salmon thrombin from the plasma includes performing an extraction process on the plasma such that:
all process temperatures are no greater than 6° C.;
no cytotoxic chemical residues remain in the one or more plasma components; and
no oxidation of plasma lipids occurs.

15. The method of claim 9, further comprising adding at least one of an antioxidant and a protease inhibitor to the plasma prior to extracting the salmon thrombin.

16. The method of claim 9, wherein the salmonid is an Atlantic salmon.

17. The method of claim 1, further comprising obtaining the salmon thrombin using recombinant technology.

18. The method of claim 1, further comprising obtaining the salmon thrombin by fractionation.

19. The method of claim 1, further comprising purifying the salmon thrombin from at least one of fresh salmon blood plasma and frozen salmon blood plasma by at least one of prothrombin precipitations and chromatographic techniques.

20. The method of claim 1, wherein the tissue damage site includes damaged soft tissue.

21. The method of claim 1, wherein administering salmon thrombin includes administering the salmon thrombin on a substrate that is not fibrinogen-based.

22. The method of claim 1, further comprising monitoring the degree of pain experienced at the site using a well-accepted and validated test for pain, after administering the salmon thrombin.

23. The method of claim 22, further comparing the degree of pain experienced at the site after administering the salmon thrombin to the degree of pain experienced at the site before administering the salmon thrombin.

24. The method of claim 22, further comprising administering salmon thrombin at the tissue damage site again if it is determined that the degree of pain experienced at the site exceeds a predetermined level as measured by a well-accepted and validated test for pain.

25. The method of claim 1, further comprising using the salmon thrombin to provide a biochemical reduction of pain experienced at the site.

26. The method of claim 1, wherein administering the salmon thrombin includes spraying the salmon thrombin.

27. A method of alleviating nociceptive pain associated with tissue damage, consisting of administering salmon thrombin at a tissue damage site, thereby diminishing a degree of pain experienced at the site, wherein diminishing a degree of pain experienced at the site includes providing analgesic relief unrelated to wound healing.

28. The method of claim 27, further comprising obtaining the salmon thrombin by one of:
obtaining a salmonid that is a progeny of domesticated broodstock that are reared under consistent and reproducible conditions, obtaining blood from the salmonid, separating plasma from the blood, and extracting the salmon thrombin from the plasma;
recombinant technology; and
fractionation.

29. A method of alleviating nociceptive pain associated with tissue damage, consisting of administering salmon thrombin at a tissue damage site, thereby diminishing a degree of pain experienced at the site, wherein diminishing a degree of pain experienced at the site includes providing analgesic relief unrelated to structural repair at the tissue damage site.

30. The method of claim 29, further comprising obtaining the salmon thrombin by one of:
obtaining a salmonid that is a progeny of domesticated broodstock that are reared under consistent and reproducible conditions, obtaining blood from the salmonid, separating plasma from the blood, and extracting the salmon thrombin from the plasma;
recombinant technology; and
fractionation.

31. A method of alleviating nociceptive pain associated with tissue damage, comprising:
blotting the tissue damage site, and
administering salmon thrombin directly to the tissue damage site to slow the rate of protease activated receptor 1 (PAR1) activation at the tissue damage site, as demonstrated by the relative rate at which salmon and human thrombin cleave tetrapeptides based on the activation sites of PAR1.

32. The method of claim 31, wherein blotting the tissue damage site includes blotting with a gauze pad.

33. The method of claim 31, wherein administering salmon thrombin includes administering more than 10 Units/ml salmon thrombin.

34. The method of claim 31, further comprising closing the tissue damage site.

35. The method of claim 34, wherein closing the tissue damage site includes suturing the site.

36. The method of claim 31, further comprising monitoring the degree of pain experienced at the site using a well-accepted and validated test for pain, after administering the salmon thrombin.

37. The method of claim 36, further comparing the degree of pain experienced at the site after administering the salmon thrombin to the degree of pain experienced at the site before administering the salmon thrombin.

38. The method of claim 36, further comprising administering salmon thrombin at the tissue damage site again if it is determined that the degree of pain experienced at the site exceeds a predetermined level as measured by a well-accepted and validated test for pain.

* * * * *